United States Patent
Gonzales et al.

(10) Patent No.: US 12,156,521 B2
(45) Date of Patent: *Dec. 3, 2024

(54) BARRIER SYSTEM

(71) Applicant: 95 Applications, L.L.C., Chandler, AZ (US)

(72) Inventors: Tony Gonzales, Chandler, AZ (US); Aaron Gonzales, Gilbert, AZ (US)

(73) Assignee: 95 Applications, L.L.C., Chandler, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/457,035

(22) Filed: Aug. 28, 2023

(65) Prior Publication Data

US 2023/0397598 A1    Dec. 14, 2023

Related U.S. Application Data

(63) Continuation of application No. 17/933,155, filed on Sep. 19, 2022, now Pat. No. 11,737,450, which is a
(Continued)

(51) Int. Cl.
*A01M 29/30* (2011.01)
*A01N 25/02* (2006.01)
(Continued)

(52) U.S. Cl.
CPC ............. *A01M 29/30* (2013.01); *A01N 25/02* (2013.01); *A61K 8/585* (2013.01); *A61K 8/891* (2013.01);
(Continued)

(58) Field of Classification Search
CPC ......... Y10T 428/24335; Y10T 428/263; E04B 1/72; A01M 29/00; A01M 1/00;
(Continued)

(56) References Cited

U.S. PATENT DOCUMENTS

| | | |
|---|---|---|
| 3,236,015 A | 2/1966 | Rubenstein |
| 4,923,698 A | 5/1990 | Rodero |
| | (Continued) | |

FOREIGN PATENT DOCUMENTS

| | | |
|---|---|---|
| JP | 2013099269 A | 5/2013 |
| JP | 2017074003 A | 4/2017 |
| | (Continued) | |

OTHER PUBLICATIONS

Amazon, "CloudBuyer Car Door Sill Protector Clear Universal Car Door Sill Protector Edge Guard Anti-Collision Protection Film Fits Most Cars", https://www.amazon.com/dp/B08535P2QH/ref=sspa_dk_detail_0?pd_rd_i=B08535P2QH&pd_rd_w=Hxtyk&pf_rd_p=5d846283-ed3e-4512-a744-a30f97c5d738&pd_rd_wg=GeRGB&pf_rd_r=GSJ9B0BXKFZHVRTXGCRQ&pd_rd_r=74b5a7a8-d01b-4a92-8e71-21deae8aeea7&spLa=ZW5jcnlwdGVkUXVhbGlmaWVyPUFUMzhYVE9IVIZGT0UmZW5jcnlwdGVkSWQ9QTAyODAwODQxVTJUUkVBWEtROTc0JmVuY3J5cHRlZEFkSWQ9QTEwMTg0ODJQVUVFTFZLWVY4T0Ymd2IkZ2V0TmFtZT1zcF9kZXRhaWxfdGhlbWF0aWMmYWN0aW9uPWNsaWNrUmVkaXJlY3QmZG9Ob3RMb2dDbGljaz10cnVl&th=1, 1996-2022, 13 pages.
(Continued)

*Primary Examiner* — Camie S Thompson
(74) *Attorney, Agent, or Firm* — Howard & Howard Attorneys PLLC (57) ABSTRACT

A barrier system includes a substantially vertical structure representing an exterior surface of a home. The barrier system also includes a coating layer disposed over and circumscribing at least 80% of the substantially vertical structure. The coating layer is in the form of a band and the substantially vertical structure includes an upper region above the coating layer that is free of the coating layer. The coating layer has a height of at least 0.25 inches, has a dried
(Continued)

film thickness of at least 5 mils, and has an average surface roughness ($R_a$) of less than 10 microns.

18 Claims, 8 Drawing Sheets

Related U.S. Application Data continuation of application No. 17/537,769, filed on Nov. 30, 2021, now Pat. No. 11,445,720, which is a continuation-in-part of application No. 17/010,803, filed on Sep. 2, 2020, now abandoned, which is a continuation-in-part of application No. 16/709,371, filed on Dec. 10, 2019, now Pat. No. 11,219,687, which is a continuation of application No. 16/456,464, filed on Jun. 28, 2019, now abandoned.

(60) Provisional application No. 63/241,724, filed on Sep. 8, 2021, provisional application No. 63/230,128, filed on Aug. 6, 2021, provisional application No. 63/194,625, filed on May 28, 2021, provisional application No. 63/173,889, filed on Apr. 12, 2021, provisional application No. 63/119,589, filed on Nov. 30, 2020, provisional application No. 62/691,519, filed on Jun. 28, 2018.

(51) Int. Cl.

| | | |
|---|---|---|
| *A61K 8/58* | (2006.01) | |
| *A61K 8/891* | (2006.01) | |
| *A61K 8/92* | (2006.01) | |
| *A61K 36/185* | (2006.01) | |
| *A61K 36/28* | (2006.01) | |
| *A61K 36/61* | (2006.01) | |
| *A61K 36/738* | (2006.01) | |
| *A61K 36/752* | (2006.01) | |
| *A61K 45/06* | (2006.01) | |
| *A61K 47/24* | (2006.01) | |
| *A61Q 17/04* | (2006.01) | |
| *A61Q 19/00* | (2006.01) | |
| *A61Q 19/08* | (2006.01) | |
| *B32B 37/12* | (2006.01) | |
| *C09D 163/00* | (2006.01) | |
| *E04B 1/72* | (2006.01) | |

(52) U.S. Cl.
CPC ............ *A61K 8/922* (2013.01); *A61K 36/185* (2013.01); *A61K 36/28* (2013.01); *A61K 36/61* (2013.01); *A61K 36/738* (2013.01); *A61K 36/752* (2013.01); *A61K 45/06* (2013.01); *A61K 47/24* (2013.01); *A61Q 19/00* (2013.01); *B32B 37/12* (2013.01); *C09D 163/00* (2013.01); *A61Q 17/04* (2013.01); *A61Q 19/08* (2013.01); *B32B 2309/12* (2013.01); *E04B 1/72* (2013.01)

(58) Field of Classification Search
CPC ........ A01N 25/00; A01N 25/02; B32B 37/12; A61K 8/585; A61K 8/891; A61K 8/922; A61K 36/185; A61K 36/28; A61K 36/61; A61K 36/738; A61K 36/752; A61K 45/06; C09D 163/00; A61Q 17/04; A61Q 19/08
USPC ................................. 424/405; 428/141, 334
See application file for complete search history.

(56) References Cited

U.S. PATENT DOCUMENTS

| | | | |
|---|---|---|---|
| 5,392,559 | A | 2/1995 | Long |
| 5,561,941 | A | 10/1996 | Long |
| 5,962,588 | A | 10/1999 | Iwamura et al. |
| 5,985,304 | A | 11/1999 | Van Voris et al. |
| 6,205,718 | B1 | 3/2001 | Murphy et al. |
| 6,223,463 | B1 | 5/2001 | Carlson et al. |
| 7,748,161 | B1 | 7/2010 | Jordan, Jr. |
| 8,256,044 | B1 | 9/2012 | Park |
| 8,359,784 | B2 | 1/2013 | Sommer |
| 9,253,973 | B2 | 2/2016 | McKnight |
| 9,353,646 | B2 | 5/2016 | Aizenberg |
| 11,219,687 | B1 | 1/2022 | Gonzales et al. |
| 11,445,720 | B2 * | 9/2022 | Gonzales ............... A61K 36/61 |
| 11,737,450 | B2 | 8/2023 | Gonzales et al. |
| 2008/0295446 | A1 | 12/2008 | Kennedy |
| 2008/0318034 | A1 | 12/2008 | Murakami et al. |
| 2009/0298902 | A1 | 12/2009 | Taranta |
| 2010/0210745 | A1 | 8/2010 | McDaniel et al. |
| 2012/0159874 | A1 | 6/2012 | Harrington |
| 2015/0305318 | A1 | 10/2015 | Moriarty |
| 2020/0000082 | A1 | 1/2020 | Gonzales et al. |

FOREIGN PATENT DOCUMENTS

| | | |
|---|---|---|
| KR | 20030077867 A | 10/2003 |
| WO | 2020087055 A1 | 4/2020 |

OTHER PUBLICATIONS

English language abstract for JP2013-099269A extracted from espacenet.com on Apr. 28, 2022, 1 page.
English language abstract for JP2017-074003A extracted from espacenet.com on Apr. 28, 2022, 1 page.
English language abstract for KR10-2003-0077867A extracted from espacenet.com on Apr. 28, 2022, 1 page.
International Search Report for Application No. PCT/US2021/061113 dated Mar. 22, 2022, 2 pages.
Seametal, ""Car Door Edge Safety Protector Stickers Transparent Nano Tape Auto Trunk Protector Film"", https://www.seametalco.com/products/seametal-car-door-edge-guard-protector-upgrade-auto-door-sill-protector-full-car-body-protective-film?variant=31883045634159, 2022, 3 pages.
Slippery paints: Eco-friendly coatings that cause ants to slip, Feat et al., Progress in Organic Coatings 135 (2019), pp. 331-344.
Surface Finish—Destiny Tools, accessed online Apr. 12, 2022.
U.S. Appl. No. 17/010,803, filed Sep. 2020, Gonzales et al.

* cited by examiner

BARRIER SYSTEM

CROSS-REFERENCE TO RELATED APPLICATIONS

This application is a Continuation of U.S. application Ser. No. 17/933,155 filed Sep. 19, 2022, which is a Continuation of U.S. application Ser. No. 17/537,769 filed Nov. 30, 2021, which claims priority to and the benefit of U.S. Prov. App. Ser. No. 63/241,724 filed Sep. 8, 2021; U.S. Prov. App. Ser. No. 63/230,128 filed Aug. 6, 2021; U.S. Prov. App. Ser. No. 63/194,625 filed May 28, 2021; U.S. Prov. App. Ser. No. 63/173,889 filed Apr. 12, 2021; and U.S. Prov. App. Ser. No. 63/119,589 filed Nov. 30, 2020. U.S. application Ser. No. 17/537,769 is also a Continuation-in-part of U.S. application Ser. No. 17/010,803 filed Sep. 20, 2020, now abandoned, which is a Continuation-in-part of U.S. application Ser. No. 16/709,371 filed Dec. 10, 2019, now U.S. Pat. No. 11,219,687, which is a Continuation of U.S. application Ser. No. 16/456,464 filed Jun. 28, 2019, now abandoned, which claims priority to and the benefit of U.S. Prov. App. Ser. No. 62/691,519 filed Jun. 28, 2018, all of which are hereby incorporated by reference in their entirety.

FIELD OF THE DISCLOSURE

The present disclosure relates to a barrier system to prevent passage of pests from scaling or climbing a vertically ascending structure, such as an exterior of a home or a wooden leg of a crib.

BACKGROUND OF THE DISCLOSURE

Many insects and other creatures are considered pests, and some can pose a serious threat to buildings and people. Physical barriers can be used to prevent crawling pests from entering buildings and scaling structures. However, these systems generally rely on placing a physical barrier that seals a structure and are typically bulky, expensive, and aesthetically displeasing. On the opposite end of the spectrum, insecticides may be used to help control pest populations but do not physically stop pests from entering buildings/structures. In some cases, insecticide can take days or weeks to kill a pest, during that time pests can enter homes and, in some cases, inflict harm on the residents of those homes. Furthermore, these chemical solutions are typically temporary and require repeated applications. Accordingly, there remains a need for an improved pest prevention system (i.e., a system that keeps pests from entering structures).

SUMMARY OF THE INVENTION

The present disclosure is directed to a barrier system. The barrier system includes a substantially vertical structure representing an exterior surface of a home. The barrier system also includes a coating layer disposed over and circumscribing at least 80% of the substantially vertical structure. The coating layer is in the form of a band and the substantially vertical structure includes an upper region above the coating layer that is free of the coating layer. The coating layer has a height of at least 0.25 inches, has a dried film thickness of at least 5 mils, and has an average surface roughness ($R_a$) of less than 10 microns.

The present disclosure also includes methods of forming the barrier system. One method includes applying a liquid coating to a surface of the substantially vertical structure to form the coating layer disposed over and circumscribing the substantially vertical structure. Another method includes transferring a dried coating layer to the substantially vertical structure to form the coating layer disposed over and circumscribing the substantially vertical structure.

BRIEF DESCRIPTION OF THE DRAWINGS

Advantages of the present disclosure will be readily appreciated, as the same becomes better understood by reference to the following detailed description, when considered in connection with the accompanying drawings.

DETAILED DESCRIPTION

The present disclosure provides a barrier system for preventing or reducing the likelihood of pests being able to scale a structure and gain access to upper portions of the structure. In instances where the structure is a home, the barrier system also prevents or reduces the likelihood of pests from reaching the interior of the home. Nonlimiting examples of pests include scorpions, cockroaches, spiders, etc.

The barrier system includes a substantially vertical structure and a coating layer disposed over and circumscribing the substantially vertical structure. For the purposes of this disclosure the term "substantially" within the phrase "substantially vertical structure" means a structure extending absolutely vertical with an allowed deviation of 5 degrees. For example, the substantially vertical structure may extend from 85 to 95 degrees from level ground.

The barrier system also includes a coating layer disposed over and circumscribing the majority of the substantially vertical structure. For the purposes of this disclosure, the phrase "circumscribing the majority of the substantially vertical structure" means that the coating layer circumscribes more than 50% of the structure. Typically, when the structure is a house, the coating layer may circumscribe the entire house with the exception of the doorway, the garage opening, and other barriers, such as electrical cables, water lines, meters, etc. Thus, typically, the barrier system circumscribes at least 80, 85, 90, or 95% of the vertical structure.

The coating layer has a height of at least 0.25 inches. Alternatively, the coating layer may have a height of 0.5, 1.0, 1.5, 2.0, 2.5, 2.7, 2.9, 3.1, 3.3, 3.5, 3.7, 3.9, 4.1, 4.3, or 4.5, inches. For example, when the coating layer circumscribes at least 80% of the vertical structure and has a height of 0.25 inches and the vertical structure is a house, a 0.25 inch band of the coating layer is disposed along 80% of the perimeter of the house.

Although not necessary for preventing or reducing the likelihood of pests, such as scorpions, from being able to scale a structure and gain access to upper portions of the structure, the height of the coating layer may also exceed 4.5 inches, if desired. Generally, the height of the coating layer is selected to prevent pests, such as scorpions, from being able to contact non-coated surfaces above the coating layer and grasping the non-coated surfaces to gain access across the coating layer. For example, a coating layer having a height of 2.5 inches may form a band around the majority of a perimeter of the home, with the band having gaps located at door and garage openings. In certain embodiments, the band may bend, curve, or turn, when circumscribing the structure to maintain a continuous perimeter when possible. For example, when a door is present in the structure, the band may curve around the door rather than merely leaving a gap in the vicinity of the door.

The coating layer has an average surface roughness ($R_a$) of less than 10 μm, when measured with a TR-Y-SRT-6200S Surface Roughness Gauge according to ANSI/ASME B46.1. Alternatively, the average surface roughness may be less than 9, 8, 7, 6, or 5 μm. Typically, the average surface roughness ($R_a$) of less than 10 μm, is sufficient to prevent or reduce scorpions and other pests from climbing up the surface of the coating layer. Without being held to any particular theory, when the coating layer has an average surface roughness ($R_a$) of less than 10 μm, the coating layer has a solid, slick "glass-like" surface that cannot be scaled by the hook-based mobility found in scorpions and other pests, as well as claws and limbs of insects and mammals. In other words, the surface of the coating layer is extremely smooth and many pests, such as scorpions and cockroaches, are unable to scale this smooth surface because their mode of mobility is unable to grasp the coating or penetrate the coating. As a result, the pests (e.g., scorpions) are kept at the ground level and unable to gain access to certain seams, holes, or transitions of material commonly found in a home. In embodiments where the structure is not a home, the pests are kept from reaching areas where their presence is undesired. For example, when the structure is the leg of a crib, the coating layer prevents the pests (e.g. scorpions) from scaling the legs of a crib to reach the mattress supported by the crib.

The coating layer is typically formed by applying a liquid coating. Although not required, typically the liquid coating is applied at a wet film thickness of at least 10 mils. Multiple passes/coats may be used to build the wet film thickness. Applying the liquid coating at a wet film thickness of at least 10 mils allows the coating to self-level and form the coating layer with an average surface roughness ($R_a$) of less than 10 μm. Depending on the substrate, greater wet film thickness may be needed to allow the wet coating to self-level and overcome the roughness and/or porosity of the substrate. For example, wet film thickness of 24 mils may be needed to overcome rough substrates, such as weathered cinder blocks. The coating layer may be applied by any suitable application method, such as roll applying, brush applying, or spray applying.

Typically, the liquid coating includes at least 40 wt. % of solid content, based on the total weight of the liquid coating. In other words, the liquid coating typically has a percent solid of 40 wt. %, which results in the coating having a high viscosity. The high viscosity is also particularly advantageous because it allows a relatively high amount of liquid coating (e.g., 12 mils or greater) to be applied without sagging. If sagging was to occur, it would likely increase the surface roughness and thus decrease the ability of the barrier system to prevent pests from scaling/climbing across the coating layer. In certain embodiments, the liquid coating has a percent solid of 42, 44, 46, 48, 50, 52, 54, or 56 wt. %, based on the total weight of the liquid coating.

Although not required, the liquid coating typically has a viscosity greater than 300 mm$^2$/s when measured in accordance with ASTM D4212-99. Alternatively, the viscosity of the liquid coating may be from 300 to 1,200, 400 to 1,200, 500 to 1,200, 600 to 1,200, 700 to 1,200, 800 to 1,100, 900 to 1,100 or about 1,000, mm$^2$/s. In addition, although not required, the coating layer typically has a gouge and scratch hardness of at least 2H, when measured in accordance with ASTM D3363-20 using a Wolff-Wilborn pencil.

As a result of the relatively high wet film thickness of the liquid coating and the fact that the wet coating typically has a percent solid of at least 40 wt. %, the coating layer has a dried film thickness of at least 5 mils. Generally, the relatively high percent solid content contributes to the high viscosity of the liquid coating which results in a liquid coating that resists sagging while maintaining its ability to self-level on a substantially vertical structure. Along these lines, the ability to self-level at high wet film thicknesses without sagging establishes the low average surface roughness ($R_a$) of the coating layer. Thus, relatively higher dried film thickness values are associated with relatively lower average surface roughness values (i.e., the greater the thickness, the smoother the surface).

In an alternative embodiment, the coating layer may be applied to the substantially vertical structure as a pre-dried and/or pre-cured coating layer. In other words, in this embodiment, the coating layer is dry to the touch before the dried coating layer is transferred to the substantially vertical structure. In this embodiment, the coating layer may have an adhesive applied to an underside of the coating layer to adhere the coating layer to the substantially vertical structure. For example, the coating layer may have a pressure sensitive adhesive applied to the underside of the coating layer. Of course, in the alternative, the adhesive may be applied directly to the substantially vertical structure before the dried coating layer is transferred to the substantially vertically structure. Although not required, a primer may also be applied prior to the adhesive. When the coating layer is transferred to the substantially vertical structure via an adhesive, the coating layer may be generally referred to as a high-performance tape or more simply a tape.

The manner in which the dried coating layer is transferred to the substantially vertical structure is not particularly limited. For example, as an alternative to the adhesive described above, the dried coating layer may be mechanically attached to the substantially vertical structure via inserting and then feeding the dried coating layer into a track system that was previously installed on the substantially vertical structure. As another alternative to the pressure sensitive adhesive described above, the adhesive of the coating layer may also be activated by heating.

It is to be appreciated that the chemistry of the dried coating layer may be any of the chemistries described within this disclosure. It is to be further appreciated that the dried coating layer should be formed to have the surface roughness described within this disclosure. Finally, although the film thickness of the coating layer is typically over 5 mils, lower film thickness are expressly contemplated while being able to achieve the desired surface roughness. For example, it is known in the art that a coating can be cast on a carrier film (e.g. biaxially oriented PET) having a smooth surface (i.e., a surface roughness within the scope of this disclosure). The resulting surface of the coating layer that mates with the carrier film will obtain the surface roughness of the carrier film as the coating layer dries or cures against the carrier film. An adhesive may then be applied to the opposite surface of the dried coating layer and the carrier film may be removed. The carrier film may also remain with the dried coating layer during storage of the dried coating layer, particularly if the dried coating layer is coiled and includes an adhesive. Thus, during application of the dried coating layer, once the carrier film is removed, the mating surface may have the requisite surface roughness for deterring pests and scorpions while having a dried film thickness of less than 5 mils. For example, the dried film thickness of the carrier layer may be from 0.5 to 35, 1 to 30, 1 to 20, 1 to 15, 1 to 10, 1 to 5, 2 to 4, or about 3, or from 15 to 35, 20 to 35, 25 to 35 or about 30, mils.

Without departing from the present disclosure, it is also contemplated that the dried coating layer may be dry to the touch but not completely cured upon its application to the substantially vertical structure. Within this particular embodiment, the coating layer may be fully cured after the dried coating layer is transferred. Suitable methods to complete the full cure of the dried coating layer include the use of a UV lamp, particularly when the chemistry of the dried coating layer is acrylic based. Of course, heat or forced air may also be used to fully cure the coating later after the coating layer is applied to the substantially vertical structure.

Although the chemistry of the coating is not particularly limited, provided the coating layer has the requisite height, thickness, and average surface roughness ($R_a$), the coating layer may include an acrylic polymer. In certain embodiments, the acrylic polymer may be further defined as a copolymer of styrene and 2-ethylhexylacrylate. The copolymer of styrene and 2-ethylhexylacrylate is typically present in an amount of from about 40 to about 60 wt. % based on the total weight of the liquid coating. The liquid coating may also include dimethyl carbonate from 40 to 60 wt. % for use as a solvent. Alternatively, the liquid coating may include a solvent blend of petroleum naphtha as a light aromatic in an amount of less than 50 wt. %, 1-2-4 trimethylbenzene between in an amount of from 5 to 25 wt. %, 1-3-5 trimethylbenzene in an amount of from 0-6 wt. %, xylene in an amount of from 0 to 15 wt. %, each based on the total weight of the liquid coating. The coating layer may also include other additives, such as $CaCO_3$, which generally further increases the viscosity of the liquid coating.

In other embodiments as an alternative to the copolymer of styrene and 2-ethylhexylacrylate, the acrylic coating may include poly(methyl methacrylate-co-butyl acrylate-co-methacrylic acid). In further alternative embodiments, the coating layer may be a blend of epoxy and silicone resins (i.e., an epoxy silicone coating). In addition, as further alternatives, polyurethanes may also be used as the base chemistry of the coating layer.

In still further embodiments, the coating layer of the barrier system may be formed from a water-based coating. The chemistry of the water-based coating is not particularly limited. For example, the water-based coating may include acrylates, polyurethanes, epoxy, etc. In one embodiment, the water-based coating for use in the barrier system is an acrylic emulsion with a glass transition temperature of about 23° C. Although not required, multiple coats of the water-based coating may be used to reach the desired film thickness. For example, 2, 3, 4, 5, or even 6 successive applications of the water-based coating may be used to reach the desired film thickness and surface roughness.

In embodiments where the water-based coating for use in the barrier system is the acrylic emulsion, the coating may also include one or more rheology modifiers. Suitable rheology modifiers include, APEO-free, solvent-free, hydrophobically modified ethylene oxide urethane (HEUR) rheology modifiers.

The barrier system may also include a pesticide applied directly on the coating layer or below the coating layer. In certain embodiments, the pesticide may include a polymeric component. Although not required, the polymeric component may encapsulate an active ingredient of the pesticide. Although not required, the polymeric component of the pesticide may be the same type of polymeric component included in the coating layer. For example, when the coating layer includes an acrylic polymer, the pesticide may be formulated to include an acrylic polymer. It is to be appreciated that the coating layer and the pesticide may both include acrylic polymers, but the precise acrylic polymer may be different. For example, the coating layer may include 2-ethylhexylacrylate and the pesticide may include an acrylate that is different than 2-ethylhexylacrylate, but the coating layer and the pesticide are still both considered to include acrylic polymers.

Without being held to any particular theory, it is believed that the coating layer assists with the retention of pesticide and prolongs the usable life of the pesticide. This is particularly desirable because not only does the coating layer prevent or reduce the ability of pests to scale/climb across its surface, but the coating layer also decreases the overall amount of pesticide that is required for a particular application, by reducing the frequency of the application of pesticide. In other words, when the pesticide is applied to the coating layer and a non-coated substrate (e.g., brick or cinder block) the pesticide continues to be active on the coating layer for a longer period of time when compared to non-coated or conventionally coated substrates. Thus, to maintain active pesticide on the non-coated substrate or the conventionally coated substrate, the pesticide must be reapplied more frequently as compared to the coating layer of the barrier system of the present disclosure.

In addition, when the pesticide is applied below the coating layer, the coating layer still functions to increase the practical effectiveness of the pesticide, because as pests attempt and fail, to climb up the coating layer, the pests fall/slide back into the pesticide and thus the amount of time that the pests dwell in the pesticide is greater in comparison to a non-coated structure. For example, scorpions may quickly pass through an area adjacent to a structure that has been treated with a pesticide and quickly ascend up a structure and out of the pesticide. However, when the structure includes the coating layer of this disclosure, the scorpion will reenter, sometimes repeatedly, the pesticide treated area as the scorpions fail and struggle to climb the coating layer. Thus, it has been surprisingly found that the coating layer having a height of merely 0.25 inches can increase the effectiveness of a pesticide applied below the coating layer.

Figure 1:
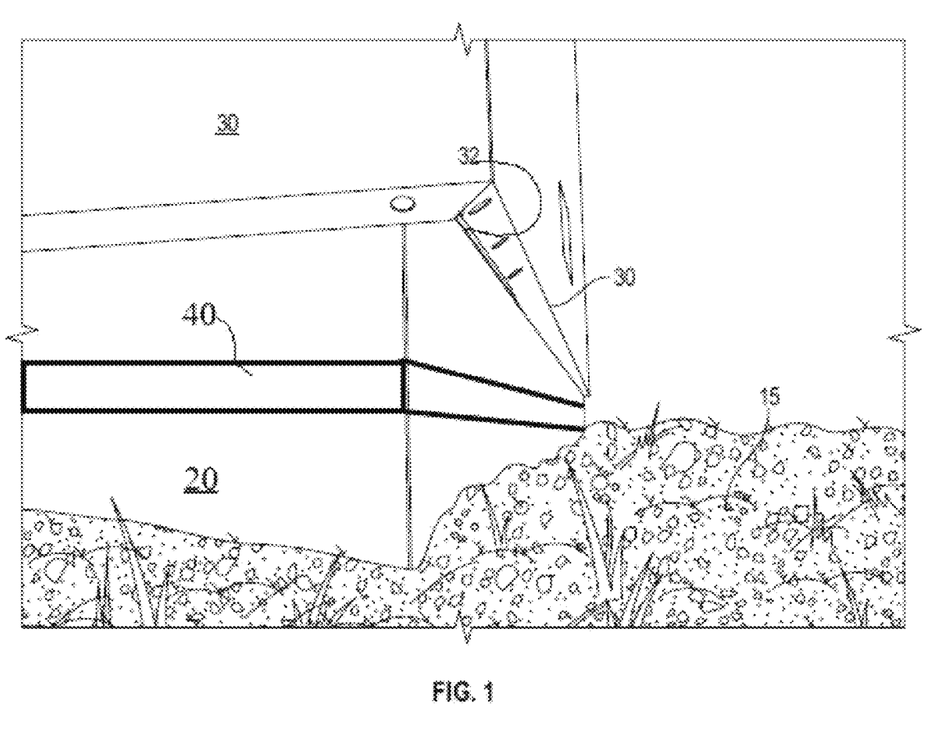
FIG. 1 illustrates a substantially vertical structure with a coating layer disposed thereof.

Referring now to the figures, as shown in FIG. 1, the coating layer 40 may be applied to exposed foundation 20 in typical masonry/stucco homes. The exposed foundation 20 may emerge over the ground level 15 and expose approximately two to six inches of mostly vertical foundation 20, or flashing. Flashing may be exposed concrete, or other treatments, such as metal plating, paint, etc. The ground 15 is often set back at two- or four-degree slope to prevent liquid build up against the foundation 20 by allowing drainage away from the building structure. Additionally, the building 30 sits upon the foundation 20 and is set above the ground level to prevent flooding, but also to provide a minor barrier to crawling pests. However, it is known that the concrete often used for foundations provides a suitable surface to allow crawling pests, including scorpions, to access the building through recesses 32, holes, cracks, etc. planned or otherwise imperfections that inevitably occur in the building. While neurotoxins and other pesticides may be applied around the house, or on the foundation, the present invention provides a physical barrier specially formulated and structured to prevent pests from climbing over the coating layer (e.g., the crawling of scorpions by ungues). The coating layer 40 acts as a permanent flashing against the foundation 20.

The liquid coating is preferably applied by brush application. Although not required, multiple coats of the liquid coating may be applied to achieve the desired wet film thickness. Typically, when multiple coats are used to apply the liquid coating, the liquid coating is applied in two, three, or four coats.

Alternatively, the liquid coating may also be applied by spraying. The spray gun used to spray apply may be powered by an air compressor attached to a high velocity/low pressure sprayer (HVLP) (such as a gravity-feed spray gun). The air compressor is preferably set at thirty psi. The low pressure is often required to limit or prevent splash and bouncing of acrylic as it is applied, and is often necessary for a complete coverage as the self-leveling occurs to provide a proper and complete coverage to the surface. Gravity guns may be preferred as they include more clearance below the spray head.

The site is preferably prepared for application of spray coating by removal of vegetation and large objects to a distance from structure by at least two feet. Previously painted surfaces may require cleaning to be free of residues, oily film, and loose paint chips. Wire brushing and washing the surface are also preferred prior to application.

Figure 6:
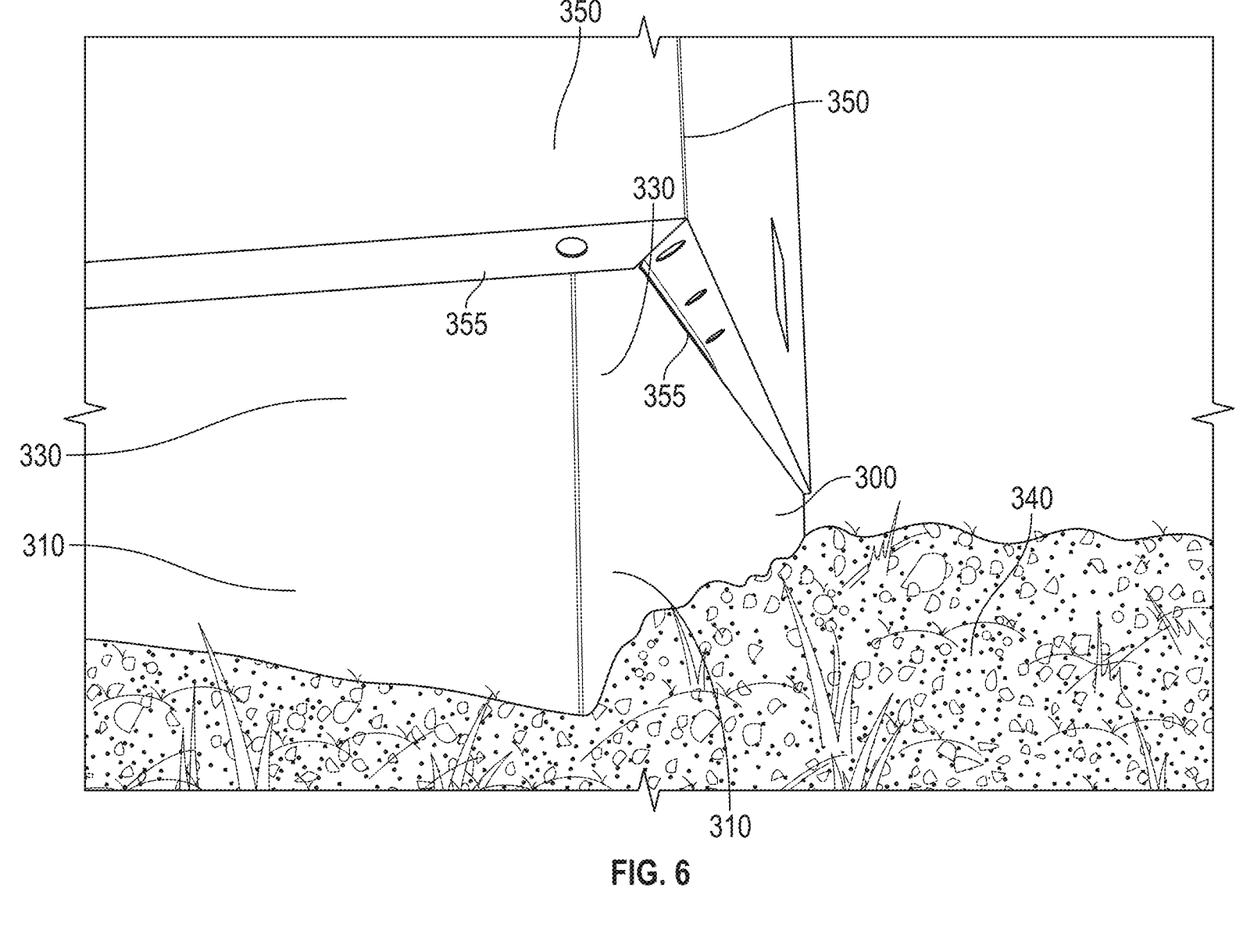
FIG. 6 illustrates a structure with exposed flashing.

Additionally, a second stripe may be painted, coated, sprayed, or otherwise applied in parallel with the stripe or otherwise (e.g. on walls and around doors, etc.) around the structure. In a preferred case, a four-inch exposed foundation flashing will be coated with a three-inch-wide acrylic stripe next to (and possibly adjacent, and possibly overlapping) a pesticide shield/barrier stripe (e.g. one inch in width). It is contemplated that any treatments will be conducted on cleaned surfaces, and if possible, the acrylic treatment will either be applied first, or if applied earlier, will be wiped and cleaned after application of other treatments. For instance, as seen in FIG. 6, acrylic barrier 310 is applied to foundation 300 in approximately a three-inch-wide (tall) stripe around corner 302. Additional pesticide treatment barrier 330 is applied as a one-inch-wide stripe there above. A ground treatment barrier 340 may also be applied to the surface. Where a 3.5 inch or wider acrylic stripe is preferred, pesticide barrier may also be applied to underside 355 of jutted building corner wall 350.

Surface preparation is critical. Previously painted surfaces must be thoroughly cleaned and free of residues, oily film, and loose paint chips.

Figure 2:
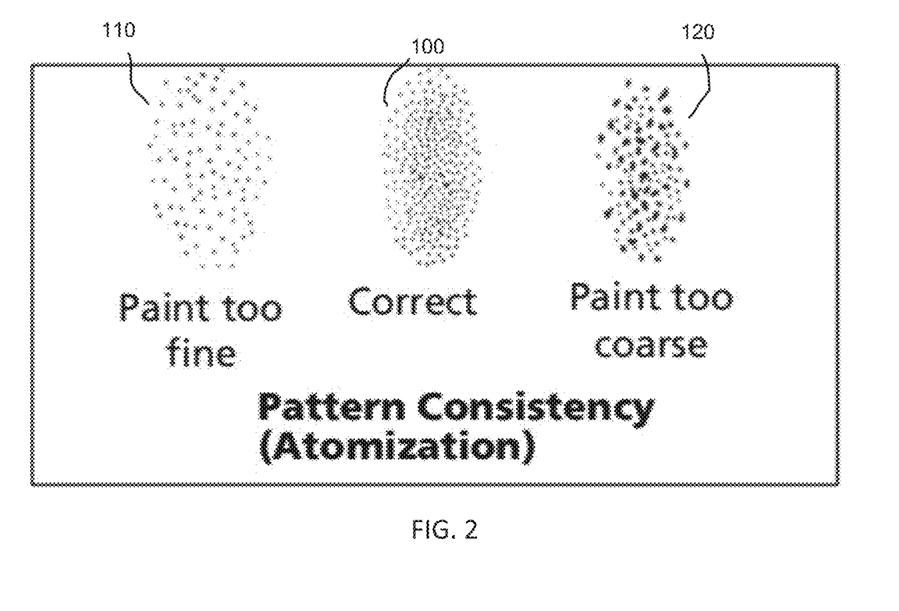
FIG. 2 illustrates various spray patterns on a surface.

As shown in FIG. 2, when spray applying, an appropriate spray pattern should be applied to the surface. Fine patterns 110 will fail to provide adequate coverage and may lead to untreated surface, while coarse patterns 120 may lead to a lumpy or inconsistent surface that may provide a foothold for pests to climb. Only a proper correct pattern 100 executed under appropriate pressure will result in the expected level surface treatment necessary to prevent passage of crawling scorpions, other pests, and the like.

Figure 3:
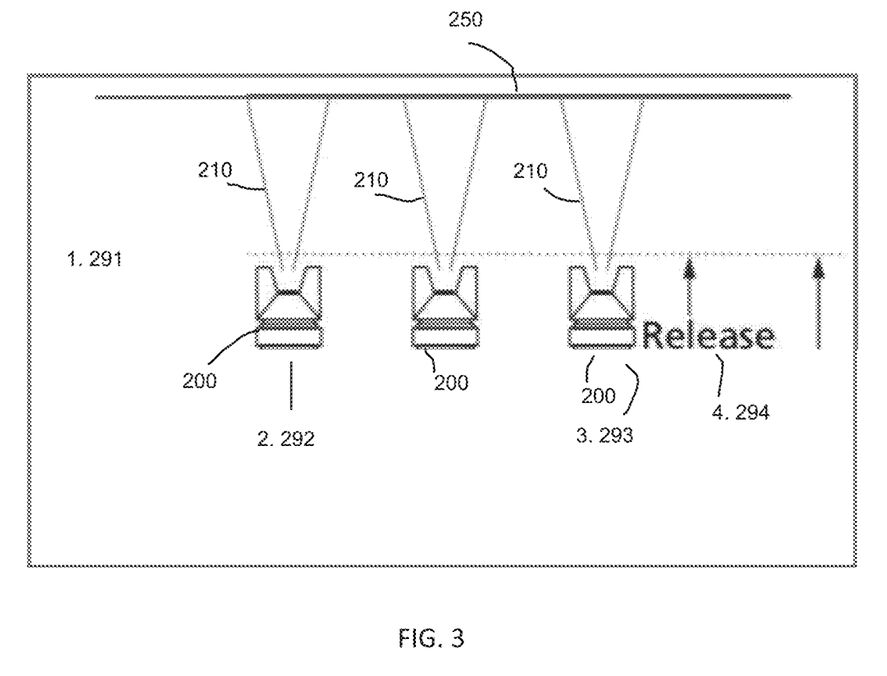
FIG. 3 illustrates a top view of the spray application process.
Figure 4:
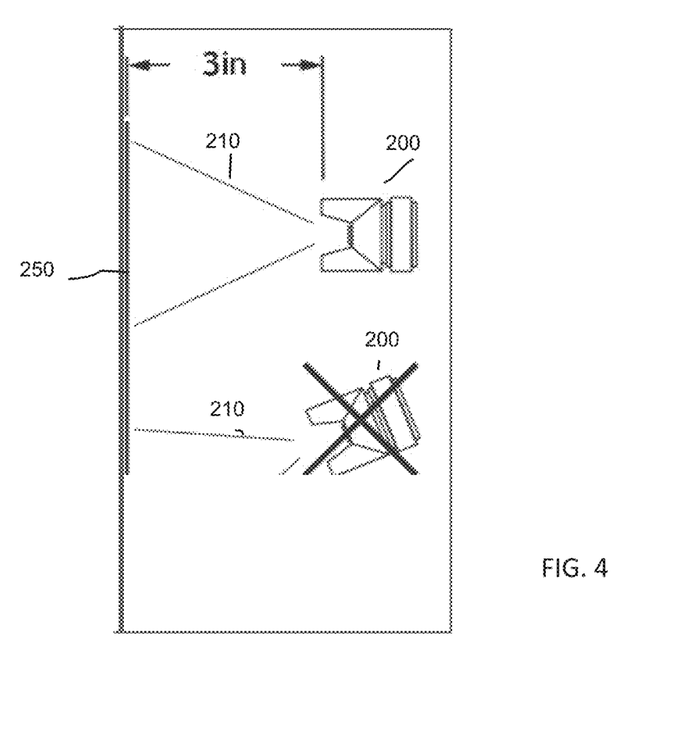
FIG. 4 illustrates a top view of an alternative spray application process.

As seen in FIGS. 3 and 4, appropriate spray distance and angle should be approximately three inches from the surface and angle deviation from perpendicular should be minimized. Spray head 200 emits spray 210 to treat surface 250. Spray head 200 should be aligned to provide a tall emission (up/down with occluded sides (left/right) as is known in the art. A proper method of treating the surface includes a stroke. First the stroke is started by initiating horizontal movement 291, then the trigger is pulled initiating the spray 292, the movement horizontally should be consistent in speed. While still moving horizontally and maintaining proper distance (approx. 3 inches) the trigger is released 293. Movement continues during the release 293. Movement is then later ended and the stroke is completed 294. Distance may be modified as needed depending on conditions, temperature, humidity, wind, surface features, and viscosity of fluid. To modify the height of application, it is preferable to begin a stroke at a different height. Alternatively, up/down motion may be applied. Preferably, for up/down motion, the spray head is adjusted and rotated ninety-degrees to provide spray pattern.

The spray should cover at least 0.25 inches and preferably 3.5 inches in vertical height along the vertical surface. The barrier is intended to prevent climbing of pests. Application is preferably close to the ground on a mostly smooth surface. Application is preferable on exposed foundation, or flashing, seen in many stucco-finished homes.

Figure 5:
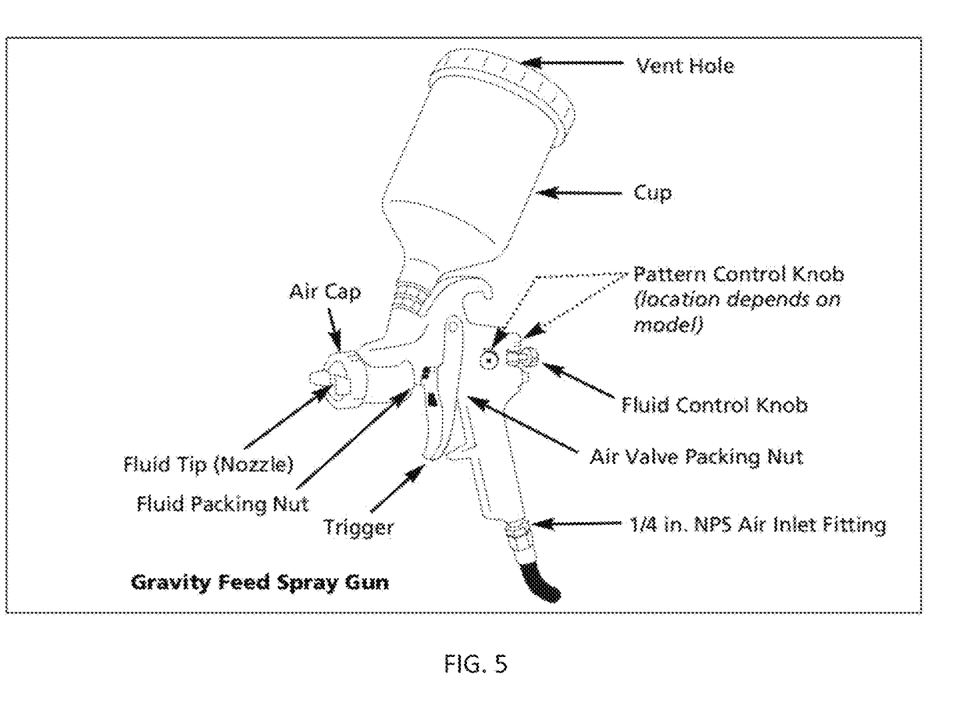
FIG. 5 illustrates a gravity spray gun as an applicator.

The essential tools for spray applying are shown in FIG. 5 and will be readily understood by one having ordinary skill in the art. A wire brush and sponge brush may be used to prepare the surface for treatment. Masking tape can be used to protect the structure and ground, and otherwise prevent inadvertent coating of surfaces meant to be kept clean. In addition to essential tools, other equipment may be utilized in the treatment process. A compressor is powered via an extension cord (preferably retractable to prevent tripping an interference with spray). Hoses provide fluid connections to the compressor, and mixture, and other fluids. The spray gun may be set up to mix the thinner solution (such as mineral spirits, etc.) with the acrylic in the gun prior to spray head release.

Brushes can be used to prepare surfaces, along with dish soap plastic covering around treated area and tape. Application user should use protective gear such as a body suit, goggles, respirator, and shoe coverings. A pump sprayer may be used with a soap solution, or other cleaning solution (including plain water) to prepare and/or clean-up site.

In preparing for the treatment, one may use a degreaser such as TSP to remove stubborn oil or grease, which is followed by rinsing thoroughly to remove residual degreaser. Power-washing, sanding or blasting is recommended but not required on clean well-prepared surfaces. The clear surface may then be etched with an appropriate chemical. Concrete may continue to leach lime even after it has cured so etching is preferred. Allow to dry thoroughly and wait at least 48 hours or test for moisture to ensure dryness. One test may incite taping edges of a clear plastic sheet to the surface and waiting a few hours. If moisture is evident, it is too wet. Wait until there is no sign of moisture before proceeding.

In some applications, multiple coatings may be used. Applying a first pass of a liquid coating seals the substrate and serves as a primer coat. A second coat may be applied, and if so, should be applied evenly avoiding heavy build up. Alternatively, the second, potentially third, fourth and more coats may be applied on the same day, including after a few minutes, hours, or immediately after the previous application.

Preferably, the spray gun is customized to spray out the relatively thick material. Spray gun may utilize a customized tip. The container may be set below the gun to the bottom.

Preferably, the spray tip is customized. In particular, a 3.5 mm tip has been found to produce good results. Standard high-volume, low pressure (HVLP) Gravity Spray guns are not known to provide a tip that large. Standard, 1.4 mm-2.2 mm standard tips can be machined to 3.5 mm tips.

Preferably, a modified standard HVLP Gravity gun may be used. A 'normal' HVLP gravity has the application container on the top of the gun barrel; however, it may be modified so the container is on the bottom of the gun barrel adjacent to the gun trigger and handle see FIG. 7. Spray gun 400 includes cup 401 joined by threaded coupling 402. Spray tip 403 is set on the end.

Figure 7:
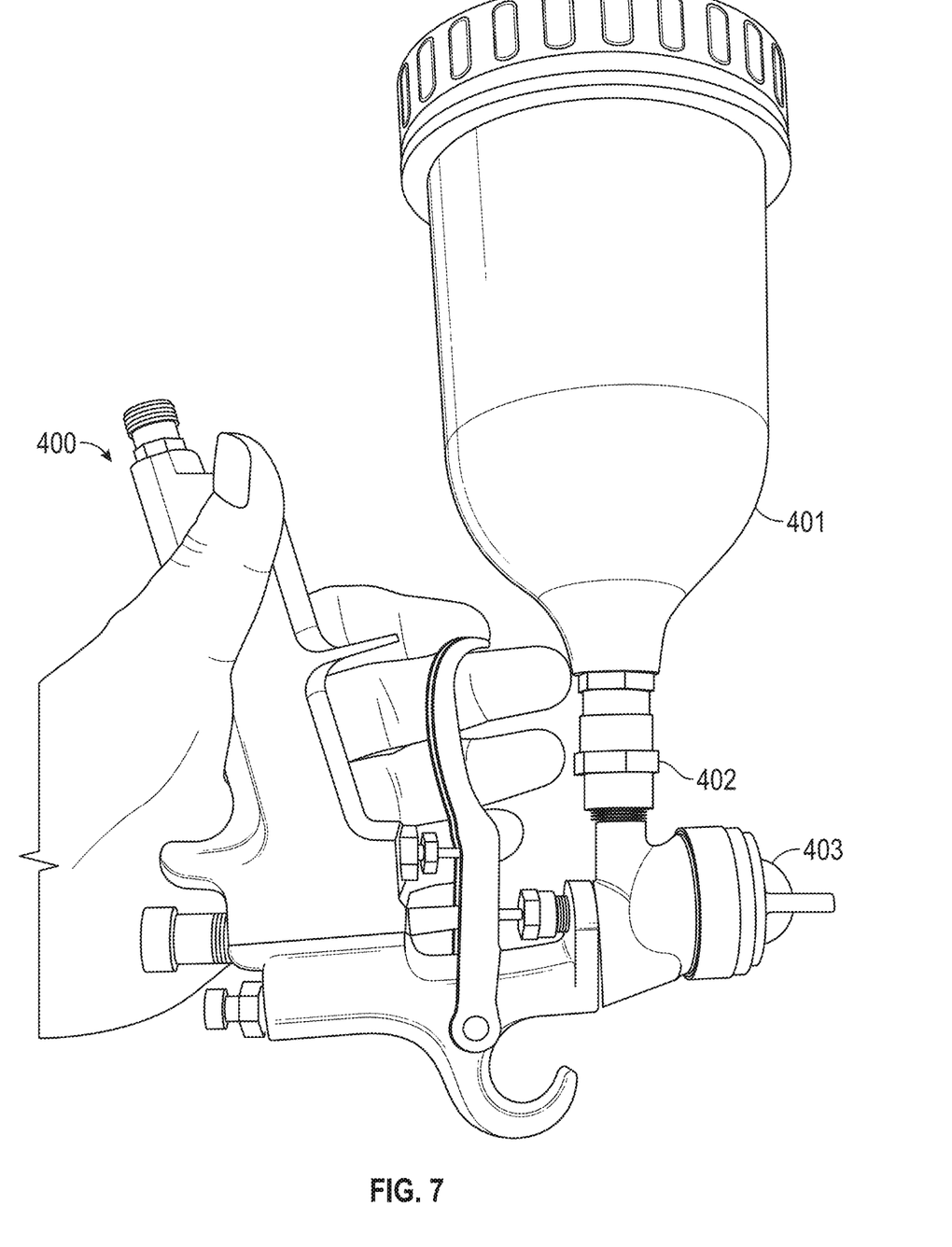
FIG. 7 illustrates a modified spray gun.
Figure 8:
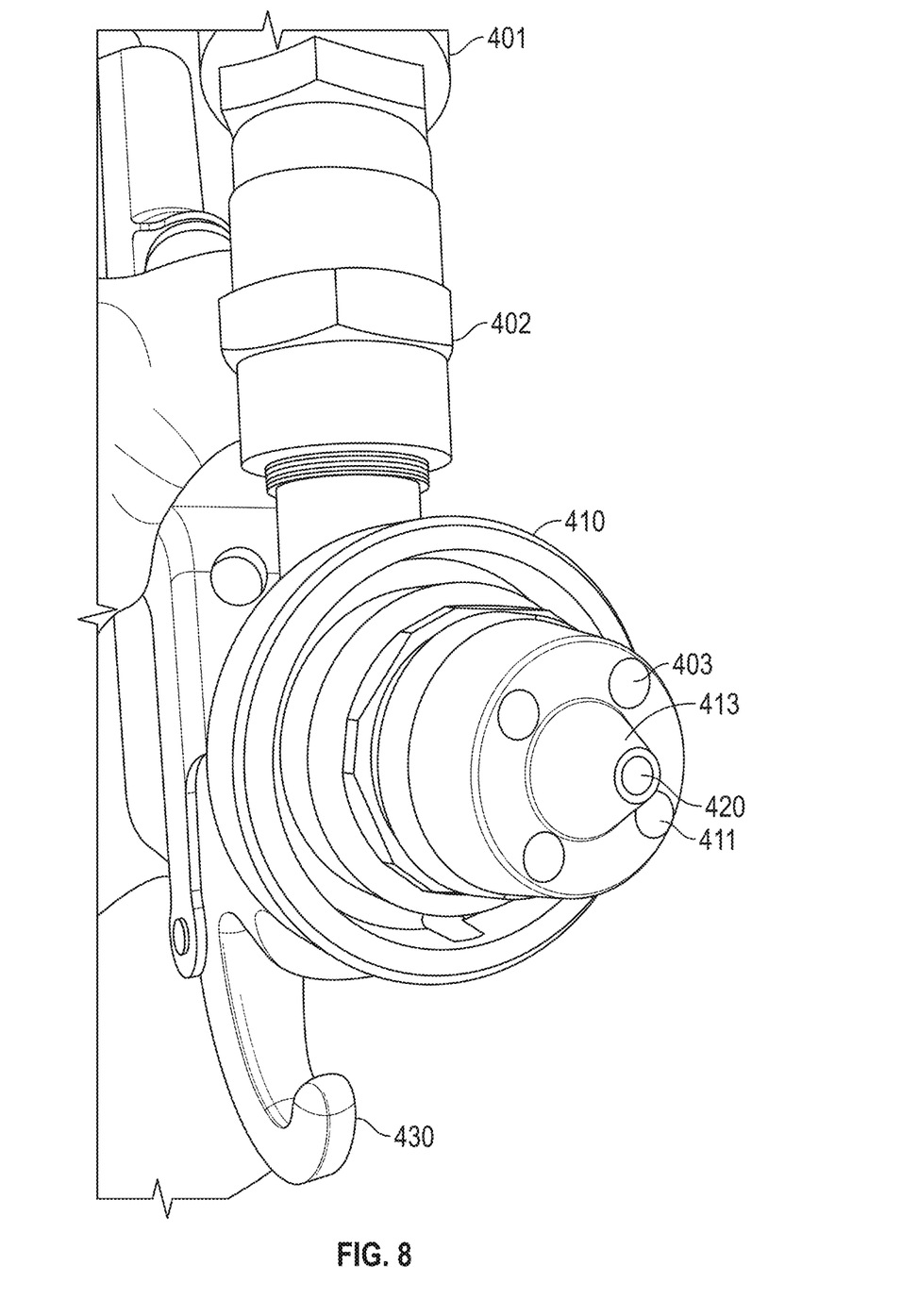
FIG. 8 illustrates a modified spray tip.

To operate a spray gun as shown in FIG. 7, a fifteen-gallon compressor having a consistent 50 psi is preferred. The spray gun should have a minimum 45 psi to drive acrylic products. A spray tip of 3 mm as shown in FIG. 8 is preferred. Cup 401 is supported by coupling 402. Tip generally includes carrier washer 410 to support spray tip 403 threadedly engaged to the washer. Spray tip 403 includes extended conical emitter 413 with machined (or wide) aperture 420 to provide for flow of material. Tip may include channels 411 to couple tip 403 to washer 410. Cup support 430 is shown for reference.

There can be instances of a 'cotton candy' also known as 'spider web' effect if there is too much pressure and/or tip is not open enough. The 'cotton candy' effect happens when the coating dries out too quickly due to excess pressure and/or spray tip is not open enough. The 'cotton candy' effect looks like thin white pieces of cotton candy floating around.

EXAMPLES

Sample bricks were coated with an acrylic based coating (hereafter the "inventive coating"), with the liquid coating applied in 2 mil increments. The acrylic was further defined as a copolymer of styrene and 2-ethylhexylacrylate. The resultant dry film thickness and average surface roughness ($R_a$) are shown below in Table I. The average surface roughness was calculated by averaging five measurements. A control sample, which was not coated, was also included.

TABLE I

| Sample No. | Wet Film Thickness (mils) | Dry Film Thickness (mils) | Average $R_a$ (μm) |
| --- | --- | --- | --- |
| Control | 0 | 0 | 25.1 |
| 1 | 2 | 1.02 | 14.9 |
| 2 | 4 | 2.88 | 13.4 |
| 3 | 6 | 4.44 | 10.4 |
| 4 | 8 | 4.96 | 10.6 |
| 5 | 10 | 5.32 | 9.0 |
| 6 | 12 | 7.04 | 9.2 |
| 7 | 14 | 8.54 | 9.1 |
| 8 | 16 | 9.88 | 8.4 |
| 9 | 18 | 10.7 | 7.3 |
| 10 | 20 | 11.24 | 6.8 |
| 11 | 22 | 13.48 | 7.0 |
| 12 | 24 | 14.82 | 6.2 |
| 13 | 26 | 15.2 | 5.1 |
| 14 | 28 | 15.86 | 5.6 |
| 15 | 30 | 16.14 | 4.5 |

The relationship between coating thickness and surface roughness when applied to a brick substrate was modeled with the logarithmic equation $y=-3.68 \ln x+15.3$. As coating thickness increased, surface roughness initially decreased at a rapid rate and then stabilized.

The samples were then evaluated for their ability to prevent scorpions from climbing up the bricks. Specifically, the samples were separately placed in a 10 gallon aquarium tank, which was heated to 33.7° C. for the purpose of simulating desert temperatures. Silicone-tipped tongs were used to transfer one scorpion to the heated tank. Tongs were used to face the scorpion towards the sample and gently prod the scorpion's opisthosoma to prompt climbing. The distance between the scorpion's posterior legs and the floor of the tank was measured 60 seconds after its first pair of legs made contact with the surface of the brick sample. This test was repeated for 20 scorpions for each sample. The results of the experiment are shown below in Table II.

TABLE II

| Scorpion No. | Control | Sample 1 (height climbed, cm) | Sample 2 (height climbed, cm) | Sample 3 (height climbed, cm) | Sample 4 (height climbed, cm) | Sample 5 (height climbed, cm) | Samples 6-15 (height climbed, cm) |
| --- | --- | --- | --- | --- | --- | --- | --- |
| 1 | 20 | 3.5 | 1 | 0 | 0 | 0.25 | 0 |
| 2 | 20 | 16 | 2.75 | 9.5 | 4.5 | 0.25 | 0 |
| 3 | 20 | 6.5 | 1.25 | 0.5 | 0 | 0 | 0 |
| 4 | 20 | 5.25 | 1.5 | 0 | 0.25 | 0 | 0 |
| 5 | 20 | 20 | 5.5 | 1.5 | 3 | 0.25 | 0 |
| 6 | 20 | 2 | 20 | 0 | 0 | 0 | 0 |
| 7 | 20 | 3 | 4 | 0 | 0 | 0 | 0 |
| 8 | 20 | 7.25 | 0.5 | 0.5 | 0 | 0 | 0 |
| 9 | 20 | 2.5 | 2 | 0.5 | 0 | 0 | 0 |
| 10 | 20 | 9.25 | 7.5 | 0.25 | 0 | 0 | 0 |
| 11 | 20 | 3.25 | 0 | 0.5 | 0 | 0 | 0 |
| 12 | 20 | 20 | 1.5 | 0 | 0.25 | 0 | 0 |
| 13 | 20 | 3 | 1 | 0 | 0 | 0 | 0 |
| 14 | 20 | 20 | 0.25 | 7 | 1.75 | 0 | 0 |
| 15 | 20 | 3.75 | 20 | 0 | 0.25 | 0.25 | 0 |
| 16 | 20 | 4.75 | 0 | 0.75 | 0 | 0 | 0 |
| 17 | 20 | 1.05 | 6 | 0 | 0.5 | 0 | 0 |
| 18 | 20 | 3.5 | 4.5 | 7 | 0 | 0 | 0 |
| 19 | 20 | 1.5 | 0 | 0.5 | 7.5 | 0.25 | 0 |
| 20 | 20 | 20 | 1.5 | 0.25 | 0 | 0.25 | 0 |

The above data shows that each and every of the 20 scorpions climbed to the top of the control. In addition, the data demonstrates that obtaining an average surface roughness of less than 10 μm was extremely effective in preventing scorpions from climbing to a height over 2.5 inches. In fact, not a single scorpion out of the 20 scorpions was able to climb over 0.25 inches in height for any of the samples having an average surface roughness of less than 10 μm.

A second, similar set of experiments was also performed on cinder blocks. Specifically, cinder blocks were coated with a 3.2 cm vertical inventive coating layer that circumscribed the entire cinder block. In other words, unlike the previous experiment where the entire brick was coated, an inventive coating layer having a height of 3.2 cm was applied to the cinder blocks of this experiment. The liquid coating was applied in 2 mil increments. The resultant dry film thickness and average surface roughness ($R_a$) are shown below in Table III. The average surface roughness was calculated by averaging five measurements. A control sample, which was not coated, was also included for the purposes of evaluating its surface roughness.

TABLE III

| Sample No. | Wet Film Thickness (mils) | Dry Film Thickness (mils) | Average $R_a$ (μm) |
| --- | --- | --- | --- |
| Control | 0 | 0 | 42.2 |
| 16 | 2 | 1.26 | 33.6 |
| 17 | 4 | 2.22 | 26.1 |
| 18 | 6 | 3 | 25.1 |
| 19 | 8 | 4.5 | 26.4 |
| 20 | 10 | 6.36 | 20.8 |
| 21 | 12 | 8.98 | 16.0 |
| 22 | 14 | 9.14 | 14.9 |
| 23 | 16 | 10.6 | 12.8 |
| 24 | 18 | 12 | 12.8 |
| 25 | 20 | 12.54 | 12.0 |
| 26 | 22 | 12.64 | 10.1 |
| 27 | 24 | 13.96 | 9.4 |
| 28 | 26 | 14.16 | 9.1 |
| 29 | 28 | 14.4 | 9.2 |
| 30 | 30 | 15 | 9.2 |
| 31 | 32 | 15.66 | 9.1 |
| 32 | 34 | 17.24 | 8.0 |
| 33 | 36 | 18.12 | 8.5 |

15 scorpions were placed in a 10 gallon glass aquarium with a substrate of desert soil and gravel. During the day, the tank was heated to 33.7° C. with a heat lamp to simulate a natural desert environment in early summer. One hour before starting the experiment, the heat lamp was turned off, and each sample was placed in the center of the tank. A cylindrical wire cage with crickets was placed inside the hollow inner portion of the cinder block to attract the scorpions.

Video footage was recorded from 8:00-9:30 PM using an iPhone 12 Pro Max and a Sony Handycam HDR-XR260 camcorder positioned at diagonal opposite corners of the tank, each capturing two adjacent cinder block surfaces. The iPhone was used to record scorpion activity on the south and east faces of the cinder block, and the Sony camcorder was used to record the north and west faces. In order to ensure visibility of the video footage while maintaining a natural nighttime environment, the tank was kept in a dark warehouse with each end of the tank illuminated with red light. The red light was used because it is well known that scorpions have little to no visual sensitivity to this wavelength.

Footage was sped up to 32× its original speed using iMovie, and was analyzed using Apple's QuickTime Player software. The data was recorded manually by tallying the number of times each increment of coating was passed through vertically by scorpions. When collecting data from the video footage, a scorpion was considered to have climbed through a certain increment of coating when its 4th pair of legs made contact with the surface at that thickness. When a scorpion was observed climbing on a S-W or N-E corner of the block, thus visible from both cameras, data was collected only from the SE video footage to avoid counting the same scorpion in both videos. Additionally, only scorpions moving in a vertical upward direction with prosoma facing toward the top of the block were counted. Scorpions climbing downward from the top of the sample toward the floor of the tank were not counted. The results of the experiment are shown below in Table IV.

TABLE IV

| Sample No. | Dry Film Thickness (mils) | Number of times crossed vertically by scorpion (SE camera) | Number of times crossed vertically by scorpion (NW camera) |
| --- | --- | --- | --- |
| 16 | 1.26 | 15 | 16 |
| 17 | 2.22 | 13 | 12 |
| 18 | 3 | 12 | 10 |
| 19 | 4.5 | 12 | 9 |
| 20 | 6.36 | 11 | 9 |
| 21 | 8.98 | 10 | 9 |
| 22 | 9.14 | 3 | 1 |
| 23 | 10.6 | 2 | 1 |
| 24 | 12 | 1 | 1 |
| 25 | 12.54 | 1 | 1 |
| 26 | 12.64 | 1 | 1 |
| 27 | 13.96 | 1 | 1 |
| 28 | 14.16 | 0 | 0 |
| 29 | 14.4 | 0 | 0 |
| 30 | 15 | 0 | 0 |
| 31 | 15.66 | 0 | 0 |
| 32 | 17.24 | 0 | 0 |
| 33 | 18.12 | 0 | 0 |

The results of the second experiment are consistent with the first experiment, with samples having an average surface roughness of less than 10 μm being extremely effective in preventing scorpions from climbing across the inventive coating layer. In contrast to the first experiment, because the cinder block had a relatively rougher surface than the brick, a greater wet coating thickness was required for the cinder block samples to achieve the target surface roughness The viscosity of the liquid coating was also evaluated. Specifically, 190 grams of the inventive coating and 10 grams of xylene were measured into a metal can to yield a 5% dilution of the product. The product was mixed for 60 seconds to fully incorporate both liquids, stirring slowly to avoid air bubbles. The viscosity of the diluted liquid coating was measured with a Zahn dip cup #5 according to ASTM D4212-99. The diluted product was applied to a painted brick in one coat using a 2 inch synthetic paint brush. One coat was defined as two brush strokes applied horizontally, repeating this motion down the face of the brick until the entire 20×9.5 cm surface was coated. A wet film thickness comb was used to measure the thickness of the first coat. This coat was left to dry for 15 minutes. A second coat of the diluted liquid coating was applied in the same manner, and the final wet film thickness (i.e., the wet thickness of both coats) was measured. After 24 hours, the dry film thickness was measured using the Defelsko PosiTector 200 dry film thickness gauge by averaging five successive measurements. This procedure was also evaluated using increasing dilutions. However, the Zahn cup had to be changed to place the viscosity range within the calibrated range of the Zahn cup. The results of this evaluation are shown below in Table V.

TABLE V

| Liquid coating (g) | Xylene (g) | Dilution | Efflux time (s) | Viscosity (mm$^2$/s) | Zahn cup # | Wet thickness after Coat 1 (mils) | Wet thickness after Coat 2 (mils) | DFT |
|---|---|---|---|---|---|---|---|---|
| 200 | 0 | 0% | 42.823 | 984.93 | 5 | 26 | 35 | 15.2 |
| 190 | 10 | 5% | 46.93 | 461.33 | 3 | 18 | 28 | 14.58 |
| 184 | 16 | 8% | 38.083 | 357.82 | 3 | 16 | 26 | 13.88 |
| 180 | 20 | 10% | 33.73 | 306.89 | 3 | 14 | 26 | 12.26 |
| 170 | 30 | 15% | 22.053 | 170.27 | 3 | 12 | 24 | 9.62 |
| 160 | 40 | 20% | 17.07 | 112 | 3 | 10 | 18 | 8.96 |

The results of the experiment indicate that the minimum viscosity of the wet inventive coating is about 300 mm$^2$/s for the purpose of achieving an adequate film thickness with two coats.

The hardness of the inventive coating layer with a dried film thickness of 14 mils on a brick was also evaluated and compared to a control having a similar film thickness. The hardness measurements ASTM D3363-20 using a Wolff-Wilborn pencil. The control used for this experiment was a commercially available exterior paint from Behr sold under the tradename Premium Plus Exterior Satin Enamel. Surface roughness of the samples were measured using the TR-Y-SRT-6200S Surface Roughness Gauge, according to ANSI/ASME B46.1. The results are presented below in Table VI.

TABLE VI

| Coating (DFT 14 mils) | Gouge hardness | Scratch hardness | Surface roughness (μm) |
|---|---|---|---|
| Control | H | 4B | 12.04 |
| Inventive Sample | 2H | 2H | 9.09 |

Although the surface roughness and hardness values between the inventive sample and the control were somewhat close, the inventive coating layer of the present invention was harder and smoother. These samples were then used to evaluate whether the perceived closeness of the hardness and surface roughness would have an impact on the ability of the coating system to deter scorpions from scaling across the coating. To evaluate this, ten bark scorpions were added to a 10 gallon glass aquarium. The aquarium was placed in direct sunlight, heating the interior to 35° C. to simulate a natural desert environment and prompt scorpions to attempt climbing. A coated brick was placed inside the tank. The number of scorpions that had successfully climbed and adhered to the brick after 60 seconds was counted and recorded. Scorpions with all four pairs of walking legs attached to the vertical surface of the brick were counted every 60 seconds for 10 minutes to complete one trial. Three trials were completed per sample, each with a different group of 10 scorpions. The results are presented below in Tables VII (a)-(c).

TABLE VII (a)

Trial I

| Coating | 1 min | 2 min | 3 min | 4 min | 5 min | 6 min | 7 min | 8 min | 9 min | 10 min |
|---|---|---|---|---|---|---|---|---|---|---|
| Control | 1 | 0 | 0 | 0 | 0 | 3 | 3 | 3 | 3 | 3 |
| Inventive Sample | 0 | 0 | 0 | 0 | 0 | 0 | 0 | 0 | 0 | 0 |

TABLE VII (b)

Trial II

| Coating | 1 min | 2 min | 3 min | 4 min | 5 min | 6 min | 7 min | 8 min | 9 min | 10 min |
|---|---|---|---|---|---|---|---|---|---|---|
| Control | 3 | 4 | 2 | 3 | 3 | 4 | 4 | 4 | 4 | 4 |
| Inventive Sample | 0 | 0 | 0 | 0 | 0 | 0 | 0 | 0 | 0 | 0 |

TABLE VII (c)

| | Trial III | | | | | | | | | |
|---|---|---|---|---|---|---|---|---|---|---|
| Coating | 1 min | 2 min | 3 min | 4 min | 5 min | 6 min | 7 min | 8 min | 9 min | 10 min |
| Control | 0 | 2 | 2 | 1 | 1 | 1 | 0 | 0 | 0 | 0 |
| Inventive Sample | 0 | 0 | 0 | 0 | 0 | 0 | 0 | 0 | 0 | 0 |

The results shown in Tables VII (a)-(c) convincingly demonstrate the inventive sample, with a gouge hardness of 2H and a surface roughness of 9 μm, completely prevented scorpions from scaling the bricks, whereas the control sample with relatively close hardness and surface roughness values allowed a significant percentage of the scorpions to scale its surface.

A series of experiments were also conducted to evaluate the synergistic effects of pesticides when applied to the coating layer. To conduct this testing, four commercially available, but different, pyrethroid insecticides were evaluated (active ingredient disclosed in parentheses): Terro Scorpion Killer (prallethrin and esfenvalerate), Harris Scorpion Killer (deltamethrin), Cy-Kick (cyfluthrin), Onslaught Fast-Cap (prallethrin, esfenvalerate, and piperonyl butoxide). Two of the pesticides, Cy-Kick and Onslaught, are microencapsulated pesticides with a polymer coating surrounding the active ingredient. Eight enclosures were constructed, each with four clay bricks arranged in a square to form a wall and a 30.48×30.48 cm stone paver as the floor. The four bricks were held together and adhered to the paver with Quikrete mortar. The inner walls of each enclosure were coated with the inventive coating layer to prevent scorpions from escaping. Four enclosures also received 26 wet mils of the inventive coating applied to the paver floor to be used as inventive samples. The remaining four enclosures were used as controls and received a coating of Behr Premium Plus Exterior Satin Enamel paint on the floor.

Each pesticide was applied to the floor of two arenas according to the pesticides' recommended application instructions: one with the inventive coating layer and one without a coating layer. The pesticides were applied evenly to each surface until the surface was sufficiently covered and left to dry overnight before scorpions were added. Five adult bark scorpions of similar size ranging from 1.5-2.75 inches were placed inside each enclosure. Scorpion activity was filmed for 13 hours. The footage was reviewed to determine whether the inventive samples increased scorpion paralysis or death. If scorpions remained active after this time period, the enclosures were periodically checked over the next 48 hours.

Upon immediate exposure to pesticides, scorpions ran around the substrate of the enclosure. Some scorpions attempted to climb vertically up the coated brick walls of the enclosure, but none were successful. The time of paralysis for each scorpion was recorded. If a scorpion was alive and appeared able to walk as normal more than 48 hours after exposure, a result of "alive" was reported. The results are reported below in Tables VIII (a)-(d).

TABLE VIII (a)

| Inventive Coating Layer + Terro Scorpion Killer | | Control + Terro Scorpion Killer | |
|---|---|---|---|
| Scorpion | Time of paralysis (h:m:s) | Scorpion | Time of paralysis (h:m:s) |
| 1 | 02:48:36 | 1 | 02:45:36 |
| 2 | 02:57:54 | 2 | 03:48:00 |
| 3 | 03:10:12 | 3 | 04:29:24 |
| 4 | 03:14:24 | 4 | 05:33:00 |
| 5 | 04:28:12 | 5 | 05:46:12 |
| Average | 03:19:48 | Average | 04:28:30 |

On average, paralysis time was 34.8% faster when Terro Scorpion Killer was used with the inventive coating layer as compared to the control.

TABLE VIII (b)

| Inventive Coating Layer + Harris Scorpion Killer | | Control + Harris Scorpion Killer | |
|---|---|---|---|
| Scorpion | Time of paralysis (h:m:s) | Scorpion | Time of paralysis (h:m:s) |
| 1 | 02:39:36 | 1 | 02:54:36 |
| 2 | 02:42:36 | 2 | 03:15:36 |
| 3 | 03:07:48 | 3 | 03:15:36 |
| 4 | 03:43:48 | 4 | 03:28:48 |
| 5 | 03:43:48 | 5 | 03:45:36 |
| Average | 03:11:30 | Average | 03:19:48 |

On average, paralysis time was 4.4% faster when Harris Scorpion Killer was used with the inventive coating layer as compared to the control.

TABLE VIII (c)

| Inventive Coating Layer + Cy-Kick | | Control + Cy-Kick | |
|---|---|---|---|
| Scorpion | Time of paralysis (h:m:s) | Scorpion | Time of paralysis (h:m:s) |
| 1 | 00:42:19 | 1 | 00:36:02 |
| 2 | 01:24:36 | 2 | 00:53:55 |
| 3 | 01:15:00 | 3 | 01:42:00 |
| 4 | 01:17:48 | 4 | 02:03:36 |
| 5 | 01:58:48 | 5 | 02:06:36 |
| Average | 01:19:24 | Average | 01:28:21 |

On average, paralysis time was 10.84% faster when Cy-Kick was used with the inventive coating layer as compared to the control.

TABLE VIII (d)

| Inventive Coating Layer + Onslaught Fastcap | | Control + Onslaught Fastcap | |
|---|---|---|---|
| Scorpion | Time of paralysis (h:m:s) | Scorpion | Time of paralysis (h:m:s) |
| 1 | 00:42:29 | 1 | 01:11:22 |
| 2 | 00:56:93 | 2 | 01:40:30 |
| 3 | 01:08:24 | 3 | 02:04:48 |
| 4 | 01:11:58 | 4 | 02:19:34 |
| 5 | 01:15:00 | 5 | 03:12:00 |
| Average | 01:02:24 | Average | 02:04:48 |

On average, paralysis time was 98.97% faster when Onslaught Fastcap was used with the inventive coating layer as compared to the control.

In summary, the test results presented in Tables VIII (a)-(d) unexpectedly demonstrate that the coating layer of the present disclosure increases the effectiveness of pesticides applied to the coating.

To further evaluate the synergy between the coating layer of the present disclosure and pesticides, additional experiments were conducted with commercially available pesticides. A conventional coating layer was applied to the floor of the control samples. Specifically, six arenas were constructed with each arena having a concrete floor. Three of the arenas had 26 wet mils of the inventive coating layer applied to the concrete floor and three of the arenas had 5 mils of KILZ premium 3 interior/exterior primer (i.e., a conventional coating layer) applied to the concrete floor. The commercially available pesticides used in this experiment were (active ingredient disclosed in parentheses): Ortho Home Defense (Bifenthrin, Zeta-Cypermethrin), Bifen XTS (Bifenthrin), and Cyonara (Lambda-Cyhalothrin). One group of five bark scorpions ranging in size from 1.5-2.75 inches was added simultaneously to each arena. Scorpion activity was recorded via Sony camcorder for 6 hours. Paralysis time was reported. The arenas were checked for deceased scorpions for 48 hours if no paralysis was observed after 6 hours. The results are reported below in Tables IX (a)-(c).

TABLE IX (a)

| Inventive Coating Layer + Ortho Home Defense | | KILZ + Ortho Home Defense | | |
|---|---|---|---|---|
| Scorpion | Time of Paralysis (h:m:s) | Scorpion | Time of Paralysis (h:m:s) | Alive after 48 hours? |
| 1 | 02:43:48 | 1 | n/a | Yes |
| 2 | 02:46:00 | 2 | none | Yes |
| 3 | 02:46:00 | 3 | none | Yes |
| 4 | 02:51:00 | 4 | none | Yes |
| 5 | 02:58:48 | 5 | none | Yes |
| Average | 02:36:36 | Average | n/a | n/a |

TABLE IX (b)

| Inventive Coating Layer + Bifen XTS | | KILZ + Bifen XTS | | |
|---|---|---|---|---|
| Scorpion | Time of Paralysis (h:m:s) | Scorpion | Time of Paralysis (h:m:s) | Alive after 48 hours? |
| 1 | 01:58:48 | 1 | n/a | Yes |
| 2 | 02:10:28 | 2 | n/a | Yes |
| 3 | 02:28:48 | 3 | n/a | Yes |
| 4 | 02:30:00 | 4 | n/a | Yes |
| 5 | 04:45:36 | 5 | n/a | Yes |
| Average | 02:46:48 | Average | n/a | n/a |

TABLE IX (c)

| Inventive Coating Layer + Cyonara | | KILZ + Cyonara | | |
|---|---|---|---|---|
| Scorpion | Time of Paralysis (h:m:s) | Scorpion | Time of Paralysis (h:m:s) | Alive after 48 hours? |
| 1 | 00:37:46 | 1 | n/a | Yes |
| 2 | 01:02:22 | 2 | n/a | Yes |
| 3 | 01:04:02 | 3 | n/a | Yes |
| 4 | 01:22:02 | 4 | n/a | Yes |
| 5 | 01:45:04 | 5 | n/a | Yes |
| Average | 01:10:16 | Average | n/a | n/a |

As shown above in Tables IX (a)-(c), each and every scorpion within the arena was paralyzed within 3 hours of exposure. In surprisingly stark contrast, no scorpions within the control arenas were paralyzed or killed within 48 hours of exposure to the same pesticides.

Additional experiments were conducted to evaluate the effectiveness of the inventive coating layer in regard to its ability to prevent Arizona bark scorpions (*Centruroides sculpturatus*), American cockroaches (*Periplaneta americana*), Turkestan cockroaches (*Shelfordella lateralis*), and Oriental cockroaches (*Blatta orientalis*) from scaling/climbing across the coating. In particular, two identical wooden structures (24×24×18 cm) were constructed and placed into an arena. In the inventive arenas, the vertical surfaces of the wooden structure were coated with 30-40 wet mils of the inventive coating. The wooden surfaces of the control arenas were left untreated. A thin layer of baby powder was dusted on top of each structure to monitor pest activity. Additionally, a food item (dead cockroach or dog food) was placed at the center of each structure to entice the pests to attempt to climb the walls. Four individuals of each species tested were placed into the arena and were monitored daily for three days (each species was run separately). These tests were run under normal laboratory conditions (24° C.; 12:12 day/night cycle; 40% relative humidity).

Upon placing the scorpions into the arena, they immediately started to climb the untreated structure. Attempts were made to climb the structure treated with the inventive coating layer; however, the scorpions were unsuccessful. After 24 hours, the food item was removed from the untreated structure while the food item on the treated structure remained in its original location. At the end of the trial, it was apparent that the scorpions had made it to the top of the untreated structure many times as the baby powder had numerous track marks. The baby powder at the top of the structure treated with the inventive coating layer remained undisturbed and the food item was never removed. This provides evidence that the inventive coating layer acted as a physical barrier against scorpions when tested under these laboratory conditions.

As with the scorpions, all of the cockroach species were able to climb the control structures with ease. Attempts were made to climb the inventive structure, but no successful attempt was directly observed. After 72 hours, the baby powder on top of the inventive coating layer remained undisturbed in both the Turkestan and Oriental trials with substantial activity observed on the control structures. A few track marks were found on top of the inventive coating layer for the American cockroach trail, although the track marks on the corresponding control were significantly greater. The experiments conclusively demonstrated that the inventive structures significantly outperformed their corresponding controls.

The present disclosure has been described in an illustrative manner, and it is to be understood that the terminology which has been used is intended to be in the nature of words of description rather than of limitation. Many modifications and variations of the present disclosure are possible in light of the above teachings. The present disclosure may be practiced otherwise than as specifically described. The subject matter of all combinations of independent and dependent claims, both singly and multiply dependent, is herein expressly contemplated.

What is claimed is:

1. A barrier system comprising:
a substantially vertical structure representing an exterior surface of a home; and
a coating layer disposed over and circumscribing at least 80% of the substantially vertical structure, wherein the coating layer is in the form of a band and the substantially vertical structure includes an upper region above the coating layer that is free of the coating layer;
wherein the coating layer has a height of at least 0.25 inches, has a dried film thickness of at least 5 mils, and has an average surface roughness (Ra) of less than 10 microns.

2. The barrier system of claim 1 wherein a pesticide is applied on the coating layer, below the coating layer, or both.

3. The barrier system of claim 2 wherein the pesticide includes a polymeric component that encapsulates an active ingredient in the pesticide.

4. The barrier system of claim 1 wherein the coating layer comprises an acrylic polymer.

5. The barrier system of claim 4 wherein the coating layer comprises a copolymer of styrene and 2-ethylhexylacrylate.

6. The barrier system of claim 1 wherein the coating layer is formed from a liquid coating having a solid content of at least 40 wt. %, based on the total weight of the liquid coating and the liquid coating has a total wet film thickness of at least 10 microns.

7. The barrier system of claim 1 wherein the average surface roughness of the coating layer is configured to prevent pests from reaching an upper portion of the substantially vertical structure that is located above the coating layer.

8. The barrier system of claim 7 wherein the pests are scorpions, cockroaches, or both.

9. The barrier system of claim 1 wherein the coating layer increases the retention of a pesticide applied directly to the coating layer when compared to the retention of the pesticide applied directly to a substrate supporting the coating layer.

10. The barrier system of claim 1 wherein the coating layer increases the dwell time of pests in a pesticide applied below the coating layer when compared to the dwell time of pests when the pesticide is applied without the coating layer being disposed above the pesticide.

11. The barrier system of claim 1 wherein an adhesive secures the coating layer to the substantially vertical structure.

12. The barrier system of claim 1 wherein the coating layer is formed from a liquid coating having a viscosity of greater than 300 mm2/s when measured in accordance with ASTM D4212-99.

13. The barrier system of claim 1 wherein the coating layer has a height of from 0.25 to 4.5 inches and is configured to prevent pests from reaching the upper region of the substantially vertical structure.

14. The barrier system of claim 13 wherein the coating layer circumscribes 100% of the substantially vertical structure.

15. A method of forming a barrier system comprising:
applying a liquid coating to a surface of a substantially vertical structure representing an exterior surface of a home to form a coating layer disposed over and circumscribing at least 80% of the substantially vertical structure, wherein the coating layer is in the form of a band and the substantially vertical structure includes an upper region above the coating layer that is free of the coating layer; and
wherein the coating layer has a height of at least 0.25 inches, has a dried film thickness of at least 5 mils, and has an average surface roughness (Ra) of less than 10 microns.

16. The method of claim 15 wherein the coating layer:
has a height of from 0.25 to 4.5 inches and an average surface roughness (Ra) of less than 10 microns, circumscribes at least 80% of the substantially vertical structure, and
the average surface roughness of the coating layer is configured to prevent pests from reaching the upper region of the substantially vertical structure.

17. A method of forming a barrier system comprising:
transferring a dried coating layer to a surface of a substantially vertical structure representing an exterior surface of a home to form a coating layer disposed over and circumscribing at least 80% of the substantially vertical structure;
wherein the coating layer is in the form of a band and the substantially vertical structure includes an upper region above the coating layer that is free of the coating layer; and
wherein the coating layer has a height of at least 0.25 inches, has a dried film thickness of at least 5 mils, and has an average surface roughness (Ra) of less than 10 microns.

18. The method of claim 17 wherein:
the dried coating layer has a height of from 0.25 to 4.5 inches and is transferred to the substantially vertical structure via an adhesive; and
the average surface roughness of the coating layer is configured to prevent pests from reaching an upper portion of the substantially vertical structure that is located above the coating layer.

* * * * *